US010136668B2

(12) United States Patent
Van Goudoever et al.

(10) Patent No.: US 10,136,668 B2
(45) Date of Patent: *Nov. 27, 2018

(54) LOW PROTEIN INFANT FORMULA WITH INCREASED ESSENTIAL AMINO ACIDS

(71) Applicant: N.V. Nutricia, Zoetermeer (NL)

(72) Inventors: Johannes Bernard Van Goudoever, Utrecht (NL); Eline Marleen Van Der Beek, Utrecht (NL); Marieke Abrahamse-Berkeveld, Utrecht (NL); Günther Boehm, Leipzig (DE)

(73) Assignee: N.V. Nutricia, Zoetermeer (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/349,700

(22) Filed: Nov. 11, 2016

(65) Prior Publication Data

US 2017/0181460 A1   Jun. 29, 2017

Related U.S. Application Data

(63) Continuation of application No. 14/613,869, filed on Feb. 4, 2015, now Pat. No. 9,492,498, which is a continuation of application No. 13/637,332, filed as application No. PCT/NL2011/050207 on Mar. 25, 2011, now Pat. No. 8,987,196.

(30) Foreign Application Priority Data

Mar. 26, 2010   (WO) ................ PCT/NL2010/050156

(51) Int. Cl.
| | |
|---|---|
| *A61K 38/00* | (2006.01) |
| *A23L 33/175* | (2016.01) |
| *A23L 33/19* | (2016.01) |
| *A23L 33/10* | (2016.01) |
| *A61K 38/16* | (2006.01) |
| *A61K 31/702* | (2006.01) |
| *A61K 31/202* | (2006.01) |
| *A61K 38/02* | (2006.01) |
| *A23L 33/00* | (2016.01) |
| *A23L 33/12* | (2016.01) |
| *A23L 33/21* | (2016.01) |

(52) U.S. Cl.
CPC .............. *A23L 33/10* (2016.08); *A23L 33/12* (2016.08); *A23L 33/175* (2016.08); *A23L 33/19* (2016.08); *A23L 33/21* (2016.08); *A23L 33/40* (2016.08); *A61K 31/202* (2013.01); *A61K 31/702* (2013.01); *A61K 38/02* (2013.01); *A61K 38/16* (2013.01); *A23V 2002/00* (2013.01); *A23V 2200/30* (2013.01); *A23V 2200/332* (2013.01); *A23V 2250/0626* (2013.01); *A23V 2250/0628* (2013.01); *A23V 2250/0654* (2013.01)

(58) Field of Classification Search
None
See application file for complete search history.

(56) References Cited

U.S. PATENT DOCUMENTS

| | | | |
|---|---|---|---|
| 3,697,287 | A | 10/1972 | Winitz et al. |
| 4,252,822 | A | 2/1981 | Berry |
| 5,719,133 | A | 2/1998 | Schmidl et al. |
| 6,503,530 | B1 | 1/2003 | Kang et al. |
| 7,651,716 | B2 | 1/2010 | Davis et al. |
| 2002/0106436 | A1 | 8/2002 | Gohman et al. |
| 2008/0145475 | A1 | 6/2008 | Flatt et al. |
| 2010/0317562 | A1 | 12/2010 | Paolella et al. |

FOREIGN PATENT DOCUMENTS

| | | |
|---|---|---|
| DE | 10221403 A1 | 12/2003 |
| EP | 0 418 593 A2 | 3/1991 |
| EP | 0 482 715 A1 | 4/1992 |
| EP | 0 492 183 A1 | 7/1992 |
| EP | 1 557 096 A1 | 7/2005 |
| WO | WO-94/14458 | 7/1994 |
| WO | WO-2007/022968 A1 | 3/2007 |
| WO | WO-2008/054200 A2 | 5/2008 |

OTHER PUBLICATIONS

Bruzzese et al. 2009. Clinical Nutrition. 28:156-161.*
Bellomonte et al., "Protein and lipid composition of human milk and infant formulas: comparison and nutritional consequences", Ann. 1st. Super. Sanita., 1990, vol. 26, No. 2, pp. 131-140.
Hernell et al. "Nutritional evaluation of protein hydrolysate formulas in healthy term infants: plasma amino acids, hematology, and trace elements", The American Journal of Clinical Nutrition, 2003, vol. 78, pp. 296-301.
http//www.biology-online.org-bodict-index.php, "Protein", downloaded Aug. 30, 2013.
International Search Report for PCT/NL2011/050207—dated Jul. 18, 2012.
Koletzko et al., "Can infant feeding choices modulate later obesity risk?", Am. J. Clin. Nutr., 2009, vol. 89 (suppl), pp. 1502S-1508S.
McAllister et al., "Ten putative contributors to the obesity epidemic", Crit Rev Food Sci Nutr., Nov. 2009, vol. 49, No. 10, pp. 868-913.
Owen et al., "Effect of infant feeding on the risk of obesity across the life course: A quantitative review of published evidence", 2006, http://journal.9med.net/html/qikan/fckxyekx/xekyxqk/200551155/20080831170214638_221, downloaded Sep. 9, 2016.
Singhal et al., "Early Nutrition and Leptin Concentrations in Later Life," American Journal of Clinical Nutrition, 2002, vol. 75, pp. 993-999.

(Continued)

*Primary Examiner* — Shulamith H Shafer

(74) *Attorney, Agent, or Firm* — Gilberto M. Villacorta; Sunit Talapatra; Foley & Lardner LLP

(57) ABSTRACT

The present invention concerns an improved balance of the essential branched chain amino acids leucine, isoleucine and valine in infant formula.

10 Claims, No Drawings

(56) References Cited

OTHER PUBLICATIONS

Souci et al., Food Composition and Nutrition Tables—Cow's Milk, 1989, pp. 12-13.
Souci et al., Food Composition and Nutrition Tables—Tomato Juice, 1989, pp. 669-670.
Stephens, MD et al., "First-Week Protein and Energy Intakes Are Associated With 18-Month Developmental Outcomes in Extremely Low Birth Weight Infants," Pediatrics 123(5):1337-1343 (2009).
Viadel et al., "Amino acid profile of milk-based infant formulas", International Journal of Food Sciences and Nutrition, 2000, vol. 51, pp. 367-372.

* cited by examiner

LOW PROTEIN INFANT FORMULA WITH INCREASED ESSENTIAL AMINO ACIDS

CROSS-REFERENCE TO RELATED PATENT APPLICATIONS

This application is a Continuation Application of U.S. application Ser. No. 14/613,869, filed Feb. 4, 2015, which is a Continuation Application of U.S. application Ser. No. 13/637,332, filed Dec. 5, 2012, now U.S. Pat. No. 8,987,196, which is the National Phase of International Patent Application No. PCT/NL2011/050207, filed Mar. 25, 2011, published on Sep. 29, 2011 as WO 2011/119033 A1, which claims priority to International Patent Application No. PCT/NL2010/050156, filed Mar. 26, 2010. The contents of these applications are herein incorporated by reference in their entirety.

FIELD OF THE INVENTION

The present invention is in the field of infant nutrition and the content of essential branched chain amino acids thereof.

BACKGROUND OF THE INVENTION

Knowledge of essential amino acid requirement in (preterm) infants is important since excessive or deficient intake might lead to long term morbidity such as obesity (Singhal et al. (2002) Am J Clin Nutr 75:993-9) or suboptimal growth and impaired neurodevelopment outcome (Stephens et al (2009) Pediatrics 2009; 123:1337-43).

The branched-chain amino acids (BCAA) leucine (Leu), isoleucine (Ile) and valine (Val) account for 35-40% of the dietary indispensable amino acids in body protein and 14% of the total amino acids in skeletal muscle. Infant nutrition has been formulated using mother's milk, breast milk, as the most ideal composition. However, due to the different amino acid composition of protein sources used for production of infant nutrition, protein levels are most often higher compared to those in breast milk to ensure sufficient intake of BCAA.

It now becomes increasingly clear that early nutrition that is consumed by the infant has metabolic effects on the infant, also later in life, i.e. metabolic imprinting. For example WO 2008/054200 discloses that metabolic imprinting is an important mechanism in programming future health and food is specifically designed to prevent obesity later in life by giving low protein diets. Hence, diets too high or too low in protein may therefore be harmful to the infants. However, the exact requirement of essential amino acids for term and preterm infants is not known.

SUMMARY OF THE INVENTION

Historically, descriptive or gross measures like growth and nitrogen balance have been used for studying the amino acid requirements. No studies have been performed using stable isotope techniques to measure essential amino acid requirements for enteral fed infants properly. The inventors therefore investigated the essential amino acid requirement by using this preferred technique in enteral fed infants in order to determine the optimal ratio of the amino acids in a nutritional composition and to determine the absolute requirements of the three essential BCAA valine, isoleucine and leucine. The results of these studies now radically change the known concepts of the amino acid requirement. This is particularly relevant for formulas with a low concentration of protein that aim to prevent adverse metabolic imprinting effects in the infant.

The present inventors surprisingly found that the valine requirement, that is currently set on 87 mg/kg/day, should be between 100 and 175 mg/kg/day, with a preferred range between 110 and 160 mg/kg /day. Also for isoleucine and leucine increased requirements have been established by the inventors. For isoleucine it has been found to be between 100 and 160 mg/kg/day, preferably between 105 and 150 mg/kg/day; the current recommendation is 88 mg/kg/day. As the leucine requirement appeared to be comparable to the currently recommended values, the most prominent consequence of the present finding is that the ratios of these three essential brached chain amino acids has to be adapted. Preferably, the weight ratio Leu:Ile:Val is between (1.1-1.5):(0.9-1.1):1.0 Instead of the currently recommended weight ratio Leu:Ile:Val of 1.9:1.0:1.0. Thus in one embodiment, the invention concerns a nutritional composition comprising protein, digestible carbohydrates and fat, wherein the protein comprises the amino acids leucine, isoleucine and valine in a weight ratio leucine:isoleucine:valine between (1.1-1.5):(0.9-1.1):1.0. Preferably, the weight ratio Leu:Ile:Val is between (1.3-1.5):(0.9-1.1):1.0, preferably between (1.3-1.5):(0.9-1.0):1.0, preferably between 1.3:1.0:1.0 and 1.5: 0.9:1.0

A preferred composition according to the invention therefore comprises per 100 ml between 40 and 120 mg valine, preferably between 55 and 120 mg valine, preferably between 70 and 110 mg valine and between 40 and 120 mg isoleucine, preferably between 55 and 110 mg ilsoleucine, preferably between 70 and 100 mg isoleucine and between 70 and 180 mg leucine, preferably between 90 and 170 mg leucine. The composition according to the invention is intended for an infant between 0-36 months. With a preferred energy content of between 60 and 70 kcal per 100 ml, a preferred composition according to the invention comprises between 90 and 180 mg valine per 100 kcal in the total composition, preferably between 100 and 150 mg valine per 100 kcal, preferably between 105 and 121 mg valine per 100 kcal, and between 90 and 180 mg isoleucine per 100 kcal in the total composition, preferably between 95 and 170 mg, preferably between 100 and 150 mg isoleucine per 100 kcal and between 120 and 260 mg leucine per 100 kcal in the total composition, preferably between 120 and 180 mg leucine per 100 kcal, preferably between 130 and 160 mg leucine per 100 kcal. Preferably the ratio leucine:isoleucine:valine is between (1.3-1.5):(0.9-1.1):1.0

Compositions comprising the above mentioned ranges of amino acids are preferably used for enteral or parental feeding of an infant. In particular the compositions are used for preventing obesity during infancy or later in their life, while maintaining optimal growth in the period the infant is depending mainly on the composition for the protein intake.

DETAILED DESCRIPTION OF THE INVENTION

Protein content: The term 'protein content' as used in the present document can be calculated from the nitrogen content using the formula: Nitrogen content×6.25. The nitrogen content can be measured according to standard procedures known to the man skilled in the art.

Infant: The term 'infant' according to the present invention means a human with an age between 0 and 36 months, preferably between 0 and 18 months and even more preferably between 0 and 6 months. The younger the infant the more dependent the infant is on the infant formula for the protein intake. Therefore, the formula is preferred for the age group of less than 12 months or infants that due to digestive problems or allergies depend on the infant formula for their intake of protein.

Premature and/or small for gestational age infants: A premature infant relates to an infant born before the standard period of pregnancy is completed before or on 37 weeks pregnancy of the mother, i.e. before or on 37 weeks from the beginning of the last menstrual period of the mother. SGA infants are those whose birth weight lies below the 10th percentile for that gestational age. They have usually been the subject of intrauterine growth restriction (IUGR). Premature and/or SGA infants include low birth weight infants (LBW infants), very low birth weight infants (VLBW infants), and extremely low birth weight infants (ELBW infants). LBW infants are defined as infants with a weight less than 2500 g. VLBW infants as infants with a weight which is less than 1500 g, and ELBW infants as infants with a weight less than 1000 g.

Infant formula is a nutritionally complete formula comprising protein, fat, carbohydrates, and micronutrients such as vitamins and minerals. Preferably the infant formula comprises dietary fiber, nucleotides and the fatty acids arachidonic acid (AA) and docosahexaenoic acid (DHA). The term infant formula excludes human breast milk.

Good nutrition is essential for optimal growth and development in the preterm born and term born infant. Protein is an important component of adequate nutrition as it provides essential amino acids required for critical protein synthesis and growth. Nutrition is especially important during the early phase of life since protein intake in the first 4 weeks of life can have a major influence on later cognitive function and blood pressure.

The alarming increase in both prevalence and severity of obesity in children has renewed the interest of feeding pattern in infancy. High early weight gain in the first 1-2 year of life is associated with later adverse health outcomes, such as increased blood pressure, increased overweight and body fat deposition, and increased risk of diabetes. The higher protein intake in infants fed infant formula compared to breastfed children, may play a role since formula-fed children reach a higher body weight and weight for length at one year of age. Lowering the protein content of infant food might be one strategy that could contribute to decreasing these adverse effects. A good protein quality, i.e. the right amounts of nutritionally available amino acids becomes than more critical.

Classically nine amino acids are regarded as dietary essential; if these amino acids are not administered in the right proportions, protein synthesis will be reduced. The requirements of the indispensable amino acids have been determined by a number of different methods. Historically, descriptive or gross measures like growth and nitrogen balance have been used. No studies have been performed using stable isotope techniques to measure essential amino acid requirements for enteral fed infants properly.

For the vulnerable populations such as neonates, it is unacceptable to maintain a deficient diet for a long period.

Brunton et al. (1998) Curr Opin Clin Nutr Metab Care, 1(5): p. 449-53 validated a minimal invasive protocol to use the indicator amino acid oxidation (IAAO) technique in infants and children. This protocol has recently been used to determine total branched chain amino acid requirements in healthy school aged children. Requirement estimates in children were similar to the estimates in adult humans, which suggest that the experimentally derived values predominantly reflect maintenance requirements and do not take in account all the growth needs.

Current recommendations of infants 0-6 months are based the amino acid content of human milk which might be inadequate since breastfed infants have quite variable milk intakes and the breastfed infant themselves largely regulate the intake they require. The European Food and Safety Authority (EFSA) directives require infant formula to contain 88 mg valine, 92 mg isoleucine and 167 mg leucine per 100 kcal with a minimum of 60 and a maximum of 70 kcal/100ml formula, i.e. between 52.5 and 62.0 mg valine per 100 ml, 55 and 64.9 mg isoleucine and between 100 and 118 mg leucine per 100 ml formula. According to the present invention these ranges are not adequate.

According to the present invention the total protein content in infant formula is preferably between 1.3 and 1.9 g protein/100 kcal, even more preferably between 1.3 and 1.8 g protein/100 kcal, resulting in an infant formula comprising between 5.2 and 7.6% protein based on the total calories of the composition. A preferred composition comprises between 90 and 180 mg valine and between 90 and 180 mg isoleucine per 100 kcal and between 130 and 260 mg leucine per 100 kcal. For an amino acid based or protein hydrolysates based composition the preferred ranges according to the present inventions are between 105 and 120 mg valine and between 100 and 120 mg isoleucine per 100 kcal and between 130 and 160 mg isoleucine per 100 kcal since these are the ranges that come closest to the experimentally determined average amino acid requirement (see examples 1-2). For non-hydrolysed (intact) protein based compositions, these latter narrow ranges are preferably about 10% lower, preferably between 10 and 20% lower. Thus in one embodiment, for non-hydrolysed (intact) protein based compositions the preferred ranges according to the present invention are between 105 and 120 mg valine and between 100 and 120 mg isoleucine per 100 kcal and between 130 and 160 mg isoleucine per 100 kcal.

In another preferred embodiment of the present invention a nutritional composition comprises a lipid, protein and digestible carbohydrate component wherein the protein component provides between 5.0 and 7.6% of the total calories, the lipid component provides 35 to 55% of the total calories and the digestible carbohydrate component provides 30 to 60% of the total calories for the manufacture of a nutritional composition, and wherein the composition comprises per 100 ml between 40 and 110 mg valine, perferably between 40 and 70 mg valine, and between 40 and 110 mg isoleucine. Preferably the weight ratio leucine:valine is in the range from 1.1:1.0 to 1.5:1.0, more preferably in the range from 1.3:1.0 to 1.5:1.0 and the weight ratio isoleucine:valine is in the range from 0.9:1.0 to 1.1:1.0, preferably is about 1.0:1.0 which means that the amounts of lieu and Val do not necessarily have to be exactly the same, but lie within the rounded off margin of the second decimal.

Thus preferably the weight ratio leucine:isoleucine:valine is in the range from (1.1-1.5):(0.9-1.1):1.0, preferably in the range from (1.1-1.5):1.0:1.0.

Preferably the composition according to the invention is used for feeding infants that largely depend on their protein intake on the nutritional composition according to the present invention. These infants preferably have with an age range between 0 and 36 months preferably between 0 and 18 months and even more preferably between 0 and 6 months. The composition can also be used for infants suffering from (multiple) food allergies that would normally restrict their intact protein intake by using hydrolyzed protein formulas or amino acid based formulas. In addition the composition can be used for the dietary management of diseases like Phenylketonuria (PKU), maple syrup urine disease (MSUD) or Tyrosinaemia.

Normaly infants are fed 150 ml of an infant milk formula per kg body weight per day. Preferably with this feeding regimen an infant ingests the amounts of leucine, isoleucine and valine now established. Thus in one embodiment, the invention concerns a non medical use of an infant formula for feeding an infant, or a non-medical method for feeding an infant comprising administering an infant formula, wherein the infant formula comprises protein that provides leucine, isoleucine and valine in a ratio of (1.1-1.5):(0.9-1.1):1.0, and the infant formula provides between 100 and 175 mg valine per kg body weight per day, and between 100 and 160 mg isoleucine per kg body weight per day when the infant is fed 150 ml of the nutritional composition per kg body weight per day.

Protein

Protein is preferably present in the composition below 8% based on total calories of the composition. Preferably the nutritional composition comprises between 5.0 and 8.0% protein based on total calories, more preferably between 5.5 and 8.0%, and even more preferably between 5.7 and 7.6% protein based on total calories. As total calories of the composition the sum of calories delivered by the fats, proteins and digestible carbohydrates of the composition is taken. A low protein concentration ensures a lower insulin response, thereby preventing proliferation of adipocytes, especially visceral adipocytes in infants. The protein concentration in a nutritional composition is determined by the sum of protein, peptides and free amino acids. The protein concentration is determined by determining the amount of nitrogen, multiplying this with a factor 6.25. One gram of protein equals 4 kcal. Based on dry weight the composition preferably comprises less than 12 wt. % protein, more preferably between 6 to 11 wt. %, even more preferably 7 to 10 wt. %. Based on a ready-to-drink or reconstituted powder liquid product the composition preferably comprises less than 1.5 g protein per 100 ml, more preferably between 0.8 and 1.35 g per 100 ml.

The source of the protein is preferably selected in such a way that the minimum requirements for essential amino acid content are met and satisfactory growth is ensured. Hence protein sources based on cows' milk proteins such as whey, casein and mixtures thereof and proteins based on soy are preferred. In case whey proteins are used, the protein source is preferably based on acid whey or sweet whey, whey protein isolate or mixtures thereof and may include a lactalbumin and β-lactoglobulin. More preferably, the protein source is based on acid whey or sweet whey from which the caseino-glyco-macropeptide (CGMP) has been removed. Removal of CGMP from sweet whey protein or the use of acid whey advantageously reduces the threonine content. Preferably α-lactalbumin enriched whey protein is used in order to optimize the amino acid profile. Using protein sources with an optimized amino acid profile closer to that of human breast milk enables all essential amino acids to be provided at reduced protein concentration, below 8% based on based on total energy content, preferably between 5.5 and 8.0% based on total energy content provided by the protein, fat and digestible carbohydrate and still ensure a satisfactory growth.

To ensure that low levels of total protein can be reached the nutritional compositions according to the present invention preferably comprise a protein source wherein the sum of leucine, isoleucine and valine provides at least 20 wt % of the total amino acid content.

If modified sweet whey is used as the protein source, it is preferably supplemented by free arginine in an amount from 0.1 to 3 wt. % and/or free histidine in an amount from 0.1 to 1.5 wt. % based on total protein.

The proteins may be intact or hydrolysed or a mixture of intact and hydrolysed proteins although intact proteins are generally preferred. Preferably the composition comprises hydrolyzed casein and/or hydrolyzed whey protein. It was found that administration of a composition wherein the protein comprises hydrolyzed casein and hydrolyzed whey results in reduced postprandial levels of both insulin and glucose compared to the administration of a composition comprising intact casein and intact whey protein. Increased levels of both insulin and glucose indicate a form of insulin insensitivity and/or resistance in formula fed infants. The present composition preferably comprises at least 25 wt. % peptides with a chain length of 2 to 30 amino acids based on dry weight of protein. The amount of peptides with a chain length between 2 and 30 amino acids can for example be determined as described by de Freitas et al, (1993), J. Agric. Food Chem. 41:1432-1438. The present composition may include casein hydrolysate or the present composition may include whey protein hydrolysate or both. The present composition preferably includes both casein hydrolysate and whey protein hydrolysate because the amino acid composition of bovine casein is more similar to the amino acid composition found in human milk protein and whey protein is easier to digest and found in greater ratios in human milk. The composition preferably comprises at least 50 wt. %, preferably at least 80 wt. %, most preferably about 100 wt. % of a protein hydrolysate, based on total weight of the protein. The present composition preferably comprises a protein with a degree of hydrolysis of the protein between 5 and 25%, more preferably between 7.5 and 21%, most preferably between 10 and 20%. The degree of hydrolysis is defined as the percentage of peptide bonds which have been broken down by enzymatic hydrolysis, with 100% being the total potential peptide bonds present. A suitable way to prepare a hydrolysate is described in WO 01/41581.

When using amino acid based protein source it will be better predictable how much of the amino acids will actually become available to the infant. Therefore, a preferred composition according to the invention comprises amino acids as protein source. In one embodiment of the composition according to the present invention the protein consist essentially of free amino acids. A preferred embodiment is shown in example 3.

Dietary Fibers

Early differences in fecal microbiota composition in children may predict overweight (Kalliomaki et al. (2008) Am J Clin Nutr 87(3): 534-538). They showed that Bifidobacterium spp affecting both the quantity and quality of the microbiota during the first year of life was higher in number in children exhibiting a normal weight at 7 years than in children developing overweight. Without being bound by theory, the inventors believe that in addition to a low protein intake, the use of dietary fiber capable of stimulating the bifido flora will have an additional effect on preventing or treatment of obesity in infants. The dietary fibers are selected from the group consisting of fibers that can stimulate the growth of Bifidobacterium spp.

Preferably the non-digestible oligosaccharides have a DP between 2 and 60. The non-digestible oligosaccharide is preferably selected from the group consisting of fructo-oligosaccharides (including inulin), galacto-oligosaccharides (including transgalacto-oligosaccharides), gluco-oligosaccharides (including gentio-, nigero- and cyclodextrinoligosaccharides), arabino-oligosaccharides, mannan-oligosaccharides, xylo-oligosaccharides, fuco-oligosaccharides, arabinogalacto-oligosaccharides, glucomanno-oligosaccharides, galactomanno-oligosaccharides, sialic acid comprising oligosaccharides and uronic acid oligosaccharides. Preferably the present composition comprises fructo-oligosaccharides, galacto-oligosaccharides and/or galacturonic acid oligosaccharides, more preferably galacto-oligosaccharides, most preferably beta-linked galacto-oligosaccharides. In a preferred embodiment the composition comprises a mixture of β-linked galacto-oligosaccharides and fructo-oligosaccharides, more preferably in a weight ratio of 20-2:1 more preferably 12-7:1. Preferably the present composition comprises galacto-oligosaccharides with a DP of 2-10 and/or fructooligosaccharides with a DP of 2-60. The galacto-oligosaccharide is preferably selected from the group consisting of beta-linked galaco-oligosaccharides, transgalacto-oligosaccharides, galacto-oligosaccharides, lacto-N-tetraose (LNT), lacto-N-neotetraose (neo-LNT), fucosyl-lactose, fucosylated LNT and fucosylated neo-LNT. β-linked galacto-oligosaccharides are for example sold under the trademark Vivinal™ (Borculo Domo Ingredients, Netherlands). Preferably the saccharides of the galacto-oligosaccharides are β-linked, since this is also the case in human milk galacto-oligosaccharides. Fructo-oligosaccharide is a NDO comprising a chain of beta-linked fructose units with a DP or average DP of 2 to 250, more preferably 10 to 100. Fructo-oligosaccharide includes inulin, levan and/or a mixed type of polyfructan. An especially preferred fructo-oligosaccharide is inulin. Fructo-oligosaccharide suitable for use in the compositions is also already commercially available, e.g. Raftiline®HP (Orafti). Uronic acid oligosaccharides are preferably obtained from pectin degradation, more preferably apple pectin, beet pectin and/or citrus pectin. Preferably the composition comprises β-linked galacto-oligosaccharide: fructo-oligosaccharide: uronic acid oligosaccharide in a weight ratio of 20-2:1:1-3 more preferably 12-7:1:1-2.

Preferably, the composition comprises of 80 mg to 2 g non-digestible oligosaccharides per 100 ml, more preferably 150 mg to 1.50 g, even more preferably 300 mg to 1 g. Based on dry weight, the composition preferably comprises 0.25 wt. % to 5.5 wt. %, more preferably 0.5 wt. % to 4 wt. %, even more preferably 1.5 wt. % to 3 wt. %. A lower amount of non-digestible oligosaccharides will be less effective in stimulating the beneficial bacteria in the microbiota, whereas a too high amount will result in side-effects of bloating and abdominal discomfort.

A study has been done determining the stimulation of the bifidoflora in formula fed infants showing an improved bifidogenic effect of galacto-oligosaccharides and long chain inulin when they are given in combination, compared to a formula with only one dietary fiber.

Infants of 9-10 months of age where given 500 ml per day of a milk formula comprising 1.2 g beta-galacto-oligosaccharides plus long chain inulin for 1 month (group A). A control group received milk formula without beta-galacto-oligosaccharides and long chain inulin (group B). In total 138 children entered the study. The faecal flora was examined before and after this period by FISH analysis.

After the intervention time, the ratio of Bifidobacteria/total bacteria was significantly higher in group A than in group B. A preferred composition according to the invention therefore comprises a combination of beta-galacto-oligosaccharides and long chain inulin.

Fat

As explained above, the protein content of infant formula has effects on the lipid metabolism and fat deposition in infants. Also, the lipid composition of the fat in infant formula has been shown to have an important impact on the prevention of obesity, and in particular on central obesity or visceral adiposity, see for example WO2008/054208. The term 'visceral adiposity' refers to a condition with increased visceral fat mass. The term visceral adiposity is also referred to as central obesity. Visceral adiposity is typically caused by (accumulation of) excessive visceral fat mass. Visceral fat, also known as organ fat, intra-abdominal fat, peritoneal fat or central fat is normally located inside the peritoneal cavity as opposed to subcutaneous fat which is found underneath the skin and intramuscular fat which is found interspersed in skeletal muscles. Visceral fat includes mesenteric fat, perirenal fat and retroperitoneal fat.

Previous research, disclosed in WO2008/054208, showed that Medium chain fatty acids (MCFA) contribute to a reduced fat mass later in life. Therefore, in addition to the specific protein and amino acid content according to the present claims, the composition advantageously comprises MCFA.

The effect on visceral fat deposition were specifically shown when using a nutritional composition comprising (i) a LA/ALA ratio between 2 and 6 and (ii) a low LA content (<14.5 wt. % based on total fatty acids) and optionally LC-PUFA (particularly DHA). Such composition resulted in a decrease in visceral adiposity later in life.

A preferred nutritional composition therefore comprises protein, digestible carbohydrates and fat, wherein the protein comprises the amino acids leucine, isoleucine and valine in a ratio leucine:isoleucine:valine in the range from (1.1-1.5):(0.9-1.1):1.0, and the fat comprises linoleic acid and alpha linoleic acid in a ratio between 2 and 6 and the linoleic acid content is less than 14.5 wt. % based on total fatty acids. This composition could preferably be used for enteral feeding of an infant for prevention of obesity later in life.

Applications

The present nutritional composition is advantageously to be ingested by or adminstered to premature infants or small for gestational age infants and hence is intended for the enteral or parenteral treatment of premature infants or small for gestational age infants. Also the present nutritional composition, and preferably the form wherein the protein consists essentially of free amino acids, is advantageously used for the treatment of infants with a metabolic disease selected from the group PKU, MSUD and tyrosinaemia, or for the treatment of infants with a food allergy. Preferably the present nutritional composition is advantageously to be ingested by or adminstered to an infant with an age between 0 and 36 months, preferably between 0 and 24 months.

The invention also concerns the use of the nutritional composition according to the present invention for the manufacture of a medicament for the treatment of a) infants with an age between 0 and 24 months and/or b) premature infants or c) small for gestational age infants or d) infants with a metabolic disease selected from the group consisting of PKU, MSUD and tyrosinaemia or e) infants with a food allergy.

In a preferred embodiment, the present invention concerns the use of the nutritional composition according to the present invention for the manufacture of a medicament for the prevention of obesity later in life.

Also the present invention concerns the non medical use of the nutritional composition according to the present invention for the manufacture of a composition for feeding of an infant with an age in the range between 0 and 36 months.

Also the present invention concerns the non medical use of an infant formula for feeding an infant, wherein the infant formula comprises protein that provides leucine, isoleucine and valine in a ratio of (1.1-1.5):(0.9-1.1):1.0, and the infant formula provides between 100 and 175 mg valine per kg body weight per day, and between 100 and 160 mg isoleucine per kg body weight per day when the infant is fed 150 ml of the nutritional composition per kg body weight per day.

EXAMPLES

Example 1

Valine and isoleucine requirements in infant

Experimental Design

Term male infants (n=28) were enrolled in this study. They had a gestational age of 37-43 weeks, a birth weight of more than 2500 gram and their postnatal age was 28 days.

The IAAO technique (Zello et al. (1993) Am J Physiol 264:E677-85) was used to determine the requirement of valine and in a separate experiment to determine the requirement of isoleucine. This method uses an indicator that is oxidized when one essential amino acid is limiting, since there is no storage of amino acids and amino acids must be partitioned between incorporation into protein or oxidation. If the tested amino acid is deficient in the diet, this will limit protein synthesis and the indicator amino acid will be oxidized. If the dietary intake of the test amino acid increases, the oxidation of the indicator will decrease until requirement of the test amino acid is met. When intake meets the requirement then protein synthesis occurs at optimum capacity and the oxidative degradation of all other essential amino acids plateau. The requirement of the test amino acid is identified by this breakpoint.

During the study period, subjects were randomly assigned to receive graded intakes of valine ranging from 5 to 236 mg/kg day or graded intakes of isoleucine ranging from 5 to 216 mg/kg day. After adaptation to the study diet for 24 hours, baseline breath samples were obtained and a tracer protocol was started. Subjects were weighted daily, before and at the end of the tracer protocol and a head circumference was measured at the study day.

Study Formula

We used a study formula identical to regular Neocate, an amino acid based formula designed to fulfil the amino acid requirements of infants (SHS, Liverpool, UK) but without the test amino acid and with a decreased amount of phenylalanine. The amount of valine was adjusted separately as L-valine. The amount of isoleucine was adjusted separately as L-isoleucine. L-phenylalanine was supplied during the adaptation time and during the infusion of $[^{13}C]$bicarbonate to obtain a stable total intake of 166 mg/kg/d during the entire study. To make the formula isonitrogenous we added L-alanine separately. Since phenylalanine was used as an indicator and phenylalanine is hydroxylated to tyrosine before oxidation can occur, we made sure that tyrosine intake was high above present requirements. A too limited tyrosine intake might reduce recovery of $^{13}C$ label in expiratory air. To minimize the effect of feeding on the $[^{13}C]$bicarbonate plateau continuous dripfeeding was given during the $[^{13}C]$bicarbonate infusion. To minimize the discomfort for the subjects they could drink a bottle every hour during the $[1-^{13}C]$phenylalanine infusion.

Tracer Protocol

On the study day subjects received a primed (15 μmol/(kg)) continuous (10 μmol/(kg·h)) enteral infusion of $[^{13}C]$bicarbonate (sterile pyrogen free, 99% $^{13}C$ Atom Percent Excess (APE); Cambridge Isotopes, Woburn, Mass.) for 3 h to quantify individual $CO_2$ production. The labeled sodium bicarbonate infusion was directly followed by a primed (30 μmol/(kg)), continuous (30 μmol/(kg·h)) enteral infusion of $[1-^{13}C]$phenylalanine (99% $^{13}C$ APE; Cambridge Isotopes, Woburn, Mass.) for five hours by an infusion pump via the nasogastric tube. The syringes with tracers were weighted before and after infusion to determine the exact amount of tracer given during the study.

Sample Collection

Breath samples were collected at the adaptation day in the first 8 patients to determine the time needed obtain a stable background enrichment, using the direct sampling method described by Van der Schoor et al. (2004) Pediatr Res 55:50-4. At the study day baseline samples were obtained 15 and 5 minutes before starting tracer infusion. During the experiment duplicate $^{13}C$-enriched breath samples were collected every 10 minutes during the isotopic steady state of the $[^{13}C]$bicarbonate infusion starting after 1.75 hours, and every 15 minutes during the isotopic steady state of the $[1-^{13}C]$phenylalanine infusion starting after 3 hours.

Analysis and Calculations $^{13}CO_2$ isotopic enrichment in expired air was measured by isotope ratio mass spectrometry (ABCA; Europe Scientific, Van Loenen Instruments, Leiden, the Netherlands) and expressed as APE above baseline. Steady state was defined as three or more consecutive points with a slope not different from zero (p<0.05). Estimated body $CO_2$ production (mmol/(kg·h)) was calculated for each infant as described previously (Riedijk et al. (2005) Pediatr Res 58:861-4). The rate of fractional $[1-^{13}C]$phenylalanine oxidation was calculated using the following equation:

$$\text{fractional phenylalanine oxidation (\%)} = [IE_{PHE} \times i_B] / [i_{PHE} \times IE_B] \times 100\%$$

where $IE_{PHE}$ is the $^{13}C$ isotopic enrichment in expired air during $[1-^{13}C]$phenylalanine infusion (APE), $i_B$ is the infusion rate of $[^{13}C]$bicarbonate (μmol/(kg·h)), $i_{PHE}$ is the infusion rate of $[1-^{13}C]$phenylalanine (μmol/(kg·h)) and $IE_B$ is the $^{13}C$ isotopic enrichment in expired air during $[^{13}C]$bicarbonate infusion (van der Schoor et al. (2004) Gut 53: 38-43).

Statistical Analysis

Descriptive data were expressed as mean ±SD. Steady state of $^{13}CO_2$ in expired breath during the $[1-^{13}C]$phenylalanine was achieved when the linear factor of the slope was found to be not significantly different from zero (p≤0.05). The valine requirement was determined by applying a two-phase lineair regression crossover model (Ball and Bayley (1984) J Nutr 114: 1741-6; Seber GAF. Linear Regression Analysis. New York: John Wiley, 1977) on the fractional oxidation rates. The safe level of intake (upper 95% CI) was determined using the Fieller's theorem (Seber GAF. Ibid.). All statistical analyses were done using SPSS (SPSS version 15.0, Chicago, Ill., USA).

Results

All subjects achieved isotopic steady state (plateau) at both $[^{13}C]$bicarbonate and $[1-^{13}C]$phenylalanine infusion defined by the absence of a significant slope between the data points at either plateau.

The Spearmen's rank correlation coefficient between valine intake and the fractional oxidation was 0.63 (p=0.000). Using the two-phase regression analysis with the valine intake as the independent variable and the fractional oxidation of the [1-$^{13}$C]phenylalanine tracer as the dependant variables, the breakpoint was determined to be 110 mg/kg/d. The safe population intake determined by the upper 95% CI was 164.6 mg/kg/d.

The Spearmen's rank correlation coefficient between isoleucine intake and the fractional oxidation was 0.74 (p=0.000). From the two-phase regression analysis with the isoleucine intake as the independent variable and the fractional oxidation of the [1-$^{13}$C] phenylalanine tracer as the dependant variable, the breakpoint was determined to be 105 mg/kg/d. The population-safe intake determined by the upper 95% CI was 152 mg/kg/d.

Example 2

Leucine Requirement of Infants

Following the same procedure as in example 1, the leucine requirement of infants was determined.

Term male infants (n=33) were enrolled in this study. They had a gestational age of 37-43 weeks, a birth weight of more than 2500 gram and their postnatal age was 28 days.
Results
All subjects achieved isotopic steady state (plateau) at both [$^{13}$C]bicarbonate and [1-$^{13}$C]phenylalanine infusion defined by the absence of a significant slope between the data points at either plateau.

Using the two-phase regression analysis with the leucine intake as the independent variable and the fractional oxidation of the [1-$^{13}$C]phenylalanine tracer as the dependant variables, the breakpoint was determined to be 140 mg/kg/d. The safe population intake determined by the upper 95% CI was 245 mg/kg/d.

Example 3

Amino Acid Based Nutrition Suitable for Treating Allergic Infants

| NUTRIENT NAME | PER 100 kcal | |
|---|---|---|
| PROTEIN EQUIVALENT (N × 6.25) | 1.36 | g |
| NITROGEN | 0.22 | g |
| CARBOHYDRATE | 12.94 | g |
| FAT (TOTAL) | 4.75 | g |
| (MCT) | 0.19 | g |
| (LCT) | 4.28 | g |
| MINERALS | | |
| SODIUM | 24.98 | mg |
| POTASSIUM | 138.45 | mg |
| CHLORIDE | 106.96 | mg |
| CALCIUM | 96.47 | mg |
| PHOSPHORUS | 70.20 | mg |
| MAGNESIUM | 5.11 | mg |
| Ca:P RATIO | 1.37 | |
| TRACE ELEMENTS | | |
| IRON | 1.48 | mg |
| ZINC | 1.03 | mg |
| IODINE | 14.22 | µg |
| MANGANESE | 0.08 | mg |
| COPPER | 0.08 | mg |
| MOLYBDENUM | 2.97 | µg |
| SELENIUM | 2.28 | µg |
| CHROMIUM | 2.06 | µg |
| VITAMINS | | |
| VITAMIN A | 151.24 | µg |
| VITAMIN E | 1.12 | IU |
| L-ASCORBIC ACID | 21.90 | mg |
| THIAMIN | 0.11 | mg |
| RIBOFLAVIN | 0.15 | mg |
| PYRIDOXINE | 0.13 | mg |
| NIACIN | 1.16 | mg |
| PANTOTHENIC ACID | 0.60 | mg |
| MYO-INOSITOL | 25.05 | mg |
| CHOLINE | 12.42 | mg |
| VITAMIN D3 | 1.94 | µg |
| CYANOCOBALAMIN | 0.31 | µg |
| FOLACIN | 10.33 | µg |
| d-BIOTIN | 6.82 | µg |
| VITAMIN K1 | 7.23 | µg |
| NIACIN (equivalent) | 1.64 | mg |
| AMINO ACIDS | | |
| L-ALANINE | 55.4 | mg |
| L-ARGININE | 98.3 | mg |
| L-ASPARTIC ACID | 91.7 | mg |
| L-CYSTINE | 36.3 | mg |
| L-GLUTAMIC ACID | 0 | mg |
| GLYCINE | 86.5 | mg |
| L-HISTIDINE | 56.2 | mg |
| L-ISO LEUCINE | 108.5 | mg |
| L-LEUCINE | 148.4 | mg |
| L-LYSINE | 100.9 | mg |
| L-METHIONINE | 23.7 | mg |
| L-PROLINE | 105.2 | mg |
| L-PHENYLALANINE | 66.1 | mg |
| L-SERINE | 64.7 | mg |
| L-THREONINE | 72.8 | mg |
| L-TRYPTOPHAN | 29.1 | mg |
| L-TYROSINE | 66.1 | mg |
| L-VALINE | 109.7 | mg |
| L-ASPARAGINE | 0 | mg |
| L-CITRULLINE | 0 | mg |
| L-CARNITINE | 1.2 | mg |
| TAURINE | 3.3 | mg |
| L-GLUTAMINE | 134.4 | mg |
| TOTAL AMINO ACIDS | 1.46 | g |

Example 4

Infant Formula Comprising Intact Milk Proteins Amino Acids According to the Invention.

| COMPONENT | UNIT | Per 100 kcal |
|---|---|---|
| 1. Protein (equivalent) | g | 1.4 |
| 2. Carbohydrate | g | 11.7 |
| Sugars | g | 11.5 |
| 3. Fat | g | 5.12 |
| Saturates | g | 2.22 |
| 4. Fibre, dietary | g | 0.856 |
| 5. Sodium | g | 25.8 |
| D. NUTRITIONAL PROPERTIES | | |
| Energy percentages: | | |
| 1. Protein (equivalent) | En % | 5.6 |
| 2. Carbohydrate | En % | 46.4 | *

-continued

| COMPONENT | UNIT | Per 100 kcal | |
|---|---|---|---|
| 3. Fat | En % | 46.3 | |
| 4. Fibre | En % | 1.7 | |
| Total | En % | 100 | |
| E. COMPOSITION | | | |
| 1. Protein (equivalent), total | g | 1.4 | |
| Nitrogen (Protein) | g | 0.224 | |
| Animal protein | g | 1.428 | |
| Whey protein | g | 0.861 | |
| Casein | g | 0.574 | |
| isoleucine and valine each | mg | 25 | |
| 2. Carbohydrate | g | 11.7 | |
| Sugars | g | 11.5 | |
| Glucose | g | 0.4 | |
| Fructose | g | | |
| Galactose | g | 0.026 | |
| Lactose | g | 11.1 | |
| 3. Fat | g | 5.12 | |
| Vegetable | g | 5.02 | |
| Animal | g | 0.11 | |
| of which milk | g | 0.06 | |
| Saturates | g | 2.22 | |
| of which MCT | g | | |
| Monounsaturates | g | 2.06 | |
| Polyunsaturates | g | 0.84 | |
| 4. Fibre, dietary | g | 0.856 | |
| Soluble | g | 0.86 | |
| Insoluble | g | | |
| 5. Moisture/water | g | 136 | |
| F. AMINO ACID COMPOSITION | | | |
| L-Alanine | mg | 65.8 | |
| L-Arginine | mg | 46.9 | |
| L-Aspartic acid/L-Asparagine | mg | 116.2 | |
| L-Cyst(e)ine | mg | 25.2 | |
| L-Glutamic acid/L-Glutamine | mg | 263.2 | |
| Glycine | mg | 29.4 | |
| L-Histidine | mg | 33.6 | |
| L-Isoleucine | mg | 109.7 | (84.7 from protein) |
| L-Leucine | mg | 158.2 | |
| L-Lysine | mg | 136.5 | |
| L-Methionine | mg | 37.1 | |
| L-Phenylalanine | mg | 63.7 | |
| L-Proline | mg | 110.6 | |
| L-Serine | mg | 86.8 | |
| L-Threonine | mg | 86.8 | |
| L-Tryptophan | mg | 23.1 | |
| L-Tyrosine | mg | 59.5 | |
| L-Valine | mg | 114.6 | (89.6 from protein) |

*Including organic acids and polyols
ratio leucine:isoleucine:valine = 1.4:1.0:1.0

The invention claimed is:

1. An infant formula composition comprising protein, digestible carbohydrates and fat, wherein the protein comprises amino acids leucine, isoleucine and valine in a weight ratio leucine:isoleucine:valine is between (1.1-1.5):(0.9-1.1):1.0, wherein the total protein content is between 1.3 and 1.9 protein/100 kcal.

2. The infant formula composition according to claim 1 wherein the weight ratio leucine:isoleucine:valine is between (1.3-1.5):(0.9-1.1):1.0.

3. The infant formula composition according to claim 1, wherein the sum of leucine, isoleucine and valine provides at least 20 wt % of the total amino acid content.

4. The infant formula composition according to claim 1, wherein the protein comprises between 120 and 180 mg leucine per 100 kcal in the total composition, between 90 and 180 mg isoleucine per 100 kcal in the total composition, and between 90 and 180 mg valine per 100 kcal in the total composition.

5. The infant formula composition according to claim 1, wherein the protein comprises between 90 and 170 mg leucine per 100 ml in the total composition, between 70 and 100 mg isoleucine per 100 ml in the total composition and between 70 and 110 mg valine per 100 ml in the total composition.

6. The infant formula composition according to claim 1, wherein the protein is present between 5 and 8% based on total calories of the composition.

7. The infant formula composition according to claim 1, further comprising at least one bifidogenic dietary fiber selected from the group consisting of beta-linked galacooligosaccharides, transgalacto-oligosaccharides, galacto-oligosaccharides, lacto-N-tetraose (LNT), lacto-N-neotetraose (neo-LNT), fucosyl-lactose, fucosylated LNT, fucosylated neo-LNT, and xylooligosaccharides.

8. The infant formula composition according to claim 1, further comprising at least one poly-unsaturated fatty acid selected from the group consisting of arachidonic acid, docosahexaenoic acid and eicosapentaenoic acid.

9. An infant formula composition comprising leucine, isoleucine and valine in a ratio of (1.1-1.5):(0.9-1.1):1.0, and which infant formula provides between 100 and 175 mg valine per kg body weight per day, and between 100 and 160 mg isoleucine per kg body weight per day when the infant is fed 150 ml of the nutritional composition per kg body weight per day.

10. The infant formula composition according to claim 1, wherein the total protein content is between 1.3 and 1.8 g protein/100 kcal.

* * * * *